United States Patent [19]

Nienburg et al.

[11] 4,101,588

[45] Jul. 18, 1978

[54] PRODUCTION OF BIS-(DIMETHYL) ACETALS OF HEXANE DIALDEHYDES

[75] Inventors: Hans Juergen Nienburg, Heidelberg; Rudolf Kummer, Frankenthal, both of Fed. Rep. of Germany

[73] Assignee: BASF Aktiengesellschaft, Ludwigshafen am Rhein, Fed. Rep. of Germany

[21] Appl. No.: 684,401

[22] Filed: May 7, 1976

Related U.S. Application Data

[63] Continuation of Ser. No. 457,577, Apr. 3, 1974, abandoned.

[30] Foreign Application Priority Data

Apr. 7, 1973 [DE] Fed. Rep. of Germany ....... 2317625

[51] Int. Cl.$^2$ ............................................. C07C 41/00
[52] U.S. Cl. .......................... 260/615 A; 260/604 HF; 260/598; 260/611 R; 568/862; 568/865
[58] Field of Search ..................... 260/615 A, 604 HF

[56] References Cited

U.S. PATENT DOCUMENTS 3,239,566  3/1966  Slaugh .......................... 260/604 HF
3,555,098  1/1971  Olivier .......................... 260/604 HF

*Primary Examiner*—Bernard Helfin
*Attorney, Agent, or Firm*—Thompson & Shurtleff

[57] ABSTRACT

An improved process for the production of aliphatic or cycloaliphatic dialdehydes or acetals of the same by reaction of an aliphatic or cycloaliphatic conjugated diene with carbon monoxide and hydrogen in the presence of a rhodium catalyst which is modified with a tertiary phosphine or phosphite at a temperature of from 70° to 160° C and at a pressure of from 100 to 600 atmospheres, the improvement consisting in using as catalyst a rhodium complex which contains carbon monoxide, a tertiary organic phosphine or tertiary organic phosphite and a halogen atom as ligands. Aliphatic and cycloaliphatic dialdehydes or the acetals of the same are suitable for the production of the corresponding diols which may be used in the production of polymers and particularly of polyurethanes.

3 Claims, No Drawings

PRODUCTION OF BIS-(DIMETHYL) ACETALS OF HEXANE DIALDEHYDES

This is a continuation, of application Ser. No. 457,577, filed Apr. 3, 1974, now abandoned.

The invention relates to an improved process for the production of aliphatic or cycloaliphatic dialdehydes and/or acetals of the same by reaction of an aliphatic or cycloaliphatic conjugated diene with carbon monoxide and hydrogen in the presence of a rhodium catalyst which has been modified with a tertiary organic phosphine.

Hydroformylation of conjugated dienes has already been attempted many times. It has been ascertained that when cobalt carbonyl catalysts are used only a simple hydroformylation takes place with hydrogenation of the second double bond. In Tetrahedron Letters, volume 32 (1969), page 2721 et seq., it is disclosed that when rhodium which has been modified with tributyl phosphine is used dialdehydes as well as monoaldehydes are obtained from butadiene-1,3 an pentadiene-1,3. The method has the disadvantage however that at a yield of from 80 to 90% the hydroformylation product obtained only contains up to 42% molar of dialdehydes. Moreover the results obtained with the catalyst used have poor reproducibility. In view of these two disadvantages the said method has not hitherto been adopted in industry.

It is an object of the invention to provide a process in which industrially viable yields of dialdehydes or acetals of the same are achieved. It is another object of the invention to substantially suppress the formation of monoaldehydes and residues. Yet another object of the invention is to provide a process in which the catalyst can be recovered and reused several times without processing and without its activity subsiding.

In accordance with this invention these and other objects and advantages are achieved in an improved process for the production of aliphatic or cycloaliphatic dialdehydes or their acetals by reaction of an aliphatic or cycloaliphatic conjugated diene with carbon monoxide and hydrogen in the presence of a rhodium catalyst which has been modified with a tertiary phosphine or phosphite at a temperature of 70° to 160° C and at a pressure of from 100 to 600 atmospheres, wherein the improvement consists in the use as the catalyst of a rhodium complex which contains carbon monoxide, a tertiary organic phosphine or a tertiary organic phosphite and a halogen atom as ligands.

It is preferred to use as the starting material an aliphatic or cycloaliphatic conjugated diene of up to 12 carbon atoms which has hydrocarbon structure and particularly an aliphatic diene of four to 12 carbon atoms or a cycloaliphatic diene of five to 12 carbon atoms, each of hydrocarbon structure. Particularly preferred starting materials are aliphatic conjugated dienes of four to eight carbon atoms and cycloaliphatic conjugated dienes of five to eight carbon atoms in each case having hydrocarbon structure. Aliphatic conjugated dienes of four or five carbon atoms and cycloaliphatic conjugated dienes of five or six carbon atoms and particularly butadiene have acquired special significance. Examples of suitable starting materials are butadiene-1,3, pentadiene-1,3, heptadiene-1,3, isoprene, cyclopentadiene, cyclohexadiene-1,3 and cyclooctadiene-1,3.

Carbon monoxide and hydrogen are used as a rule at least in a stoichiometric amount but advantageously in an excess of up to 100 mole%. The volumetric ratio of carbon monoxide to hydrogen in the mixture of carbon monoxide and hydrogen is usually from 1:4 to 4:1 and particularly from 1:1 to 1:2.

The reaction is carried out at a temperature of from 70° to 160° C. Temperatures of from 100° to 140° C have proved to be particularly suitable. A pressure of from 100 to 600 atmospheres is maintained during the reaction. It is advantageous to use pressures of from 200 to 400 atmospheres.

The catalysts used for the reaction are rhodium complexes which contain carbon monoxide, a tertiary organic phosphine or organic phosphite and a halogen atom as ligands. Chlorine, bromine or iodine are suitable halogens, chlorine and bromine have achieved particular significance. It has proved to be advantageous for the atomic ratio of catalyst metal to halogen in the catalyst to be about 1:1.

Preferred tertiary organic phosphines or organic phosphites are those which have as organic radicals not more than two identical or different alkyls of one to twenty carbon atoms, cycloalkyls of five to 12 carbon atoms, aralkyls of seven to 10 carbon atoms and at least one aryl of six to 10 carbon atoms. The said radicals may have substituents which are inert under the reaction conditions, for example one or two hydroxyl groups, alkoxy or carbalkoxy groups of one to four carbon atoms, amino groups or halogen atoms. Examples of suitable compounds are triphenylphosphine, diethylphenylphosphine, tritolylphosphine, trinaphthylphosphine, diphenylmethylphosphine, diphenylbutylphosphine, tris(p-chlorophenyl)phosphine, tris(p-carbomethoxycarbonyl)-phosphine, tris(p-cyanophenyl)-phosphine, diphenylphosphonic acid phenyl ester, benzenephosphonic acid diphenyl ester and triphenyl phosphite.

Preferred phosphines or phosphites are triarylphosphines and phosphites whose organic radical is derived from benzene, such as triphenylphosphine, tris(p-chlorophenyl)-phosphine and triphenyl phosphite.

Rhodium complexes which are preferred as catalysts have the formula:

XRhCOL$_2$ in which

X is a chlorine atom, bromine atom or iodine atom and particularly a chlorine atom and L is one of the abovementioned phosphines or phosphites.

It is possible to use for the reaction a complex compound which has been prepared previously. In operation on an industrial scale, however, it is preferred to prepare the complex compound in situ. It has proved to be particularly suitable to produce the catalyst under the reaction conditions for example from 1 mole of rhodium trichloride, 1 mole of rhodium trioxide and an excess of phosphine or phosphite. It is advantageous to use a ratio of metal to phosphorus of from 1:2 to 1:100 and particularly from 1:5 to 1:50.

The catalysts are used as a rule in an amount of from 10 to 1000 ppm calculated as rhodium metal and based on the reaction mixture. Amounts of from 20 to 100 ppm have proved to be particularly suitable.

It has proved to be particularly advantageous to carry out the reaction in the presence of an alkanol or alkanediol as a solvent. It is preferred to use an alkanol of one to four carbon atoms or an alkanediol of two to four carbon atoms. Alkanols of one to four carbon atoms and particularly methanol have achieved special significance. Examples of suitable solvents are methanol, ethanol, propanol, n-butanol, isobutanol, ethylene glycol, propanediol-1,2, and butanediol-1,3. It is advantageous to use the alkanol or alkanediol at least in such an amount that there are two hydroxyl groups available for each formyl group to be introduced. An excess of for example 100 to 1000 mole% has proved to be suitable.

The process according to the invention may be carried out for example by placing one of the said diolefins with an alkanol or alkanediol as solvent in a high pressure vessel with the said complex catalyst, forcing in carbon monoxide and hydrogen in the said ratio and carrying out the reaction at the said temperature and pressure. After the reaction is over the solvent and hydroformylation product are separated from the residue containing the catalyst by a conventional method, for example by distillation, if necessary at subatmospheric pressure. In this treatment, the extremely good thermal stability of the said catalysts has proved to be of great value. The residue containing catalyst obtained may therefore be immediately used again for further reactions without detriment to its catalytic activity. The reaction may be carried out continuously without difficulty in a suitable apparatus.

The acetals obtained according to the process of the invention may be converted for example by treatment with water in the presence of an acid ion exchanger into aldehydes. The aldehydes may be used for example as tanning agents and in the production of resins for surface coating materials. The aldehydes and their acetals may be easily converted into the corresponding diols by hydrogenation with known hydrogenation catalysts and preferably hydrogenation catalysts containing nickel, copper, chromium, cobalt or molybdenum at temperatures of from 100° to 200° C and at pressures of from 50 to 300 atmospheres. The corresponding diols may find manifold use in the production of polymers, for example polyurethanes and polyesters, or as cross-linking agents for polymers.

The process according to the invention will be illustrated by the following examples.

EXAMPLE 1

800 ml of methanol (= 630 g), 0.5 g of ClRhCO[P($C_6H_5$)$_3$]$_2$ (= 75 mg, 0.72 × $10^{-3}$ gram atoms of Rh) and 10 g of triphenylphosphine (= 38 millimoles) are placed in a 2-liter high-pressure vessel. After the vessel has been flushed out with nitrogen 200 ml (= 120 g) of butadiene is added and an equimolar mixture of carbon monoxide and hydrogen is forced in up to a pressure of 200 atmospheres. The whole is heated to 120° C and the pressure is raised at the same time to 280 atmospheres. The pressure is maintained at from 260 to 280 atmospheres by forcing in more gas mixture until the absorption of gas ends after about 4 hours. The whole is then cooled and the discharge (879 g) is distilled off from catalyst and traces of residue (together about 20 g). The oxo product contains according to gas chromatographic analysis about 2% of valeraldehyde, 3% of dimethylacetal of 2-methylbutanal-1, 15% of the dimethylacetal of n-valeraldehyde and 80% of the bis(-dimethyl) acetals of various isomeric hexanedials. For accurate identification of the dioxo products they are hydrogenated with 50 g of Raney nickel with an addition of 100 g of water in methanol at 150° C and 280 atmospheres, distilled and esterified with acetic anhydride. The diesters of the hexanediols are then separated by gas chromatography and the following composition is thus ascertained: 10% of hexanediol-1,6, 55% of 2-methylpentanediol-1,5 and 35% of other isomers, mainly 2-ethylbutanediol-1,4.

The residue containing catalyst described above may be used again 10 times for the same reaction without any decline in the rate of reaction or any change in the composition of the product being detected. This proves the unusual stability of the catalyst.

EXAMPLES 2 to 5

Examples 2 to 5 are comparative Examples from which may be seen the advantages of the use of methanol as solvent in the oxo reaction of butadiene-1,3.

600 ml of solvent, 0.20 g of $Rh_2O_3$ and 0.17 g of $RhCl_3$ (= 2.4 × $10^{-3}$ gram atoms of Rh), 25.3 g of triphenylphosphine (= 97 millimoles) are placed in a 2-liter high pressure vessel provided with an electromagnetic reciprocating stirrer. After flushing with nitrogen 125 g of butadiene is added and a mixture of carbon monoxide and hydrogen is forced in up to a pressure of 200 atmospheres. The whole is heated to 120° C and the pressure is increased by forcing in more of the gas mixture to 280 atmospheres. As soon as the pressure during the reaction has fallen to 260 atmospheres it is raised again to 280 atmospheres by forcing in more gas mixture. The experiment is carried on until the absorption of gas is over (about 10 hours). After the reaction has ended the products are distilled off from the residue containing the catalyst and hydrogenated either with $LiAlH_4$ (hexane, ether) or with Raney nickel (ethyl acetate, methanol). The mixture of pentanols and hexanediols is then fractionally distilled.

| Example | 2 | 3 | 4 | 5 |
|---|---|---|---|---|
| Solvent | hexane | ethyl acetate | diethyl ether | methanol |
| Gas absorbed (atmospheres) | 150 | 305 | 270 | 400 |
| Oxo product (grams) | 174 | 189 | 189 | 224 |
| Distillation of hydrogenation product of (%): | | | | |
| $C_5$-ol | 52 | 42 | 33 | 20 |
| $C_6$-diol | 24 | 36 | 46 | 76 |
| Residue | 24 | 22 | 21 | 4 |

The Examples clearly show that when methanol is used the yield of dioxo products is highest, undesirable pentanols are formed to a lesser extent and also residues of high boiling point occur in considerably smaller amounts than when other solvents are used.

EXAMPLE 6

This is a comparative Example which proves the superiority of a catalyst containing halogen over the simple hydrido complex HRhCO[P($C_6H_5$)$_3$]$_3$ which can be prepared from $Rh_2O_3$.

As described in Example 1 120 g of butadiene is hydroformylated in methanol using 2.2 g of HRhCO[P($C_6H_5$)$_3$]$_3$ (= 2.4 millimoles or 2.4 × $10^{-3}$ gram atoms or Rh) and 25.2 g of triphenylphosphine as catalyst. The experiment is carried out exactly as in Example 5. Gas chromatographic investigation of the oxo product shows that the aldehydes are present to the extent of more than 90% as free aldehydes. This results in turn to a number of secondary reactions which gives undesired high boiling point byproducts (for example aldolization). The aldehydes exhibit a distribution of about 80% of monooxo product and only 20% of dioxo product.

After distillation of the crude oxo product and hydrogenation only 80 g of pentanols and 50 g of hexanediols, but 70 g of products of higher boiling point are isolated.

EXAMPLE 7

This is a comparative Example which proves the need to use high pressure for the double hydroformylation of conjugated dienes.

The procedure of Example 1 is followed, i.e. using methanol as solvent. The reaction is carried out however at a total pressure of from 30 to 50 atmospheres. As a result the reaction proceeds much more slowly and the absorption of gas is not over until after seventeen hours. The following compounds are found by gas chromatography: valeraldehyde and 2-methylbutanal-1 about 40%; the dimethylacetals of the two monoaldehydes about 35%; and the aldolization product of valeraldehyde about 12%. The remainder are small amounts of unidentified compounds. Hexanedials and their acetals are only detectable in traces (less than 3%).

EXAMPLE 8

The procedure described in Example 1 is followed. The catalyst used however is 0.535 g of BrRhCO[P($C_6H_5$)$_3$]$_2$ (= 75 mg of Rh, $0.72 \times 10^{-3}$ gram atom of Rh) and 10 g of triphenylphosphine. Hydroformylation of the butadiene is carried out at 120° C and 280 atmospheres. Absorption of gas is over about 6 hours. The oxo product is distilled off from the catalyst. It consists to the extent of 90% of methyl acetals of hexanediols according to gas chromatographic analysis. The acetals are hydrogenated with Raney nickel with the addition of water at 150° C and 280 atmospheres for better identification. Fractional distillation of the alcohols gives 220 g (= 85% of theory) of a hexanediol mixture which passes over at 125° to 140° C at 12 torr. The following composition of the diol mixture is ascertained after esterification with acetic anhydride and gas chromatographic analysis: 8% of hexanediol-1,6, 50% of 2-methylpentanediol-1,5 and 42% of other isomers.

EXAMPLE 9

The procedure described in Example 1 is repeated but the catalyst used is 0.572 g of ClRhCO[P($C_6H_5$)$_3$]$_2$ (= 75 mg of Rh) and 11.8 g of triphenyl phosphite. After hydroformylation, hydrogenation of the acetal mixture and distillation, 137 g of isomeric hexanediols (= 52% of theory) is obtained.

EXAMPLE 10

200 ml of butadiene (= 120 g) is hydroformylated as in Example 1 using 0.13 g of ClRhCO[P($C_6H_5$)$_3$]$_2$ (= 20 mg Rh, $0.19 \times 10^{-3}$ gram atom Rh) and 5 g of triphenylphosphine (= 19 millimoles). Absorption of gas is over after 8 hours. The discharge (= 880 g) is separated by distillation into the residue containing the catalyst (7g), the solvent and the oxo product. According to gas chromatographic analysis the oxo product contains 1.5% of the dimethylacetal of 2-methylbutanal-1, 16.5% of n-valeraldehyde dimethyl acetal and 82% of methyl acetals of various isomeric hexanedials.

100 g of the acetals of dialdehyde passing over at 57° to 60° C at 8 torr are stirred with 500 g of water in the presence of 50 g of a strongly acid ion exchanger (AMBERLYST 15 pA) for 2 hours at 60° C. The pale yellow solution which is now homogeneous is filtered from the ion exchanger. The solution is carefully concentrated in vacuo (50 torr) and at a bottoms temperature of 55° to 60° C until 425 g of distillate has been obtained. 170 g of a pale yellow solution of the dialdehydes in water remains behind. According to the CO number it contains about 28% of dialdehydes and according to gas chromatography is devoid of methanol and undissociated acetals.

We claim:

1. A process for production of bis-(dimethyl) acetals of hexane dialdehydes with formation of monoaldehydes and residues being substantially suppressed which comprises hydroformylation butadiene with hydrogen and carbon monoxide at a temperature of 100°–140° C and a pressure of 200–400 atmospheres in the presence of a catalytic amount in the range of 10 to 1000 ppm, calculated as rhodium metal and based on the reaction mixture, of a catalyst of the formula

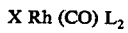

in which X is chlorine, bromine, or iodine and L is triphenylphosphine or triphenylphosphite, the ratio of Rh to P in said catalyst being in the range of 1:2 to 1:100 in methanol as the solvent, the amount of said methanol being in molar excess in the range of 100% to 1000% mol percent for each formyl group to be formed in the hydroformylation reaction.

2. A process as claimed in claim 1, wherein X in said formula is chlorine.

3. A process as claimed in claim 1 wherein the ratio of Rh to P in said catalyst is in the range of 1:5 to 1:50.

* * * * *